United States Patent
Lindhofer et al.

(10) Patent No.: US 8,663,638 B2
(45) Date of Patent: Mar. 4, 2014

(54) INTRAOPERATIVE TRIFUNCTIONAL ANTIBODY APPLICATION FOR PROPHYLAXIS OF INTRAPERITONEAL TUMOR CELL DISSEMINATION

(75) Inventors: Horst Lindhofer, Munich (DE); Markus M. Heiss, Cologne (DE)

(73) Assignee: Trion Pharma GmbH, Munich (DE)

( * ) Notice: Subject to any disclaimer, the term of this patent is extended or adjusted under 35 U.S.C. 154(b) by 338 days.

(21) Appl. No.: 12/676,133

(22) PCT Filed: Sep. 4, 2008

(86) PCT No.: PCT/EP2008/061720
§ 371 (c)(1),
(2), (4) Date: Sep. 1, 2010

(87) PCT Pub. No.: WO2009/030734
PCT Pub. Date: Mar. 12, 2009

(65) Prior Publication Data
US 2010/0322933 A1 Dec. 23, 2010

(30) Foreign Application Priority Data
Sep. 4, 2007 (EP) .................................. 07115602

(51) Int. Cl.
*A61K 39/00* (2006.01)
(52) U.S. Cl.
USPC ...................................................... 424/136.1
(58) Field of Classification Search
None
See application file for complete search history.

(56) References Cited

U.S. PATENT DOCUMENTS

| 8,277,806 | B2 | 10/2012 | Lindhofer |
| 2002/0009430 | A1* | 1/2002 | Lindhofer et al. ........... 424/93.7 |
| 2003/0223999 | A1* | 12/2003 | Lindhofer ................. 424/155.1 |

FOREIGN PATENT DOCUMENTS

| WO | WO 00/18806 A1 | 4/2000 |
| WO | WO 02/20039 A1 | 3/2002 |
| WO | WO 02/20039 A2 | 3/2002 |
| WO | WO 02/20039 A3 | 3/2002 |
| WO | WO 2004/014421 A1 | 2/2004 |
| WO | WO 2007/093630 A1 | 8/2007 |

OTHER PUBLICATIONS

Yoon et al (Immunity, 1:563-569, 1994).*
Luiten et al, (Journal of Immunotherapy, 6:496-504, 1997).*
Canaveri et al (JNCI, 19:1463-1469, 1995).*
Alegre et al (Transplantation, 52(4):674-679, 1991, abstract only).*
Ferran et al (Transplantation, 50(4):642-658, 1990, abstract only).*
Cole et al (Transplantation, 68(4):563-571, 1999, printed as pp. 1-14).*
Renders et al (CEI, 133:307-309, 2003).*
Stephenson et al., "The Systematic Inflammatory Response (SIRS)—Number and Type of Positive Criteria Predict Interventions and Outcomes in Acute Surgical Admissions," 2010, World J. Surg. vol. 34, pp. 2757-2764.
Talmor et al., "Relationship of Systemic Inflammatory Response Syndrome to Organ Dysfunction, Length of Stay, and Mortality in Critical Surgical Illness: Effect of Intensive Care Unit Resuscitation," 1999, Arch. Surg., vol. 134, pp. 81-87.
Lindhofer, H., et al., "Bispecific Antibodies Effectively Purger Cancer Cells From Peripheral Blood Stem Cell Collections without Affecting Colony Forming Units," *Annual Meeting International Society for Experimental Hematology*, vol. 25(8), p. 879 (Aug. 24, 1997).
Opitz, I., et al., "Instillation of Taurolidine/Heparin after Laparotomy Reduces Intraperitoneal Tumor Growth in a Colon Cancer Rat Model," *European Surgical Research*, vol. 39(3), pp. 129-135 (Mar. 2, 2007).
Zeidler, R., et al., "The Fc-region of a new class of intact bispecific antibody mediates activation of accessory cells and NK cells and induces direct phagocytosis of tumor cells," *British Journal of Cancer*, vol. 83(2), pp. 261-266 (Jul. 2000).

* cited by examiner

*Primary Examiner* — Brad Duffy
(74) *Attorney, Agent, or Firm* — Kilpatrick Townsend & Stockton LLP (57) ABSTRACT

The invention describes the use of trifunctional bispecific and trispecific antibodies for destroying tumor cells which e.g. are disseminated intraperitoneally due to a surgical intervention, wherein the antibody is administered intraoperatively, preferably directly locally into the abdominal cavity.

20 Claims, 1 Drawing Sheet

INTRAOPERATIVE TRIFUNCTIONAL ANTIBODY APPLICATION FOR PROPHYLAXIS OF INTRAPERITONEAL TUMOR CELL DISSEMINATION

The present application is a U.S. National Phase of PCT/EP2008/061720, filed Sep. 4, 2008, which claims the benefit of European Patent Application No. 07 115 602.0, filed Sep. 4, 2007, both of which are incorporated herein by reference.

The invention relates to the use of a trifunctional bispecific and/or trispecific antibody for the preparation of a pharmaceutical composition for destruction of e.g. tumor cells disseminated intraperitoneally due to a surgical intervention.

An as yet unsolved problem in surgical oncology is the intraoperative dissemination of tumor cells. It is accepted that during most intraabdominal tumor operations, due to the surgical intervention detachment and dissemination of tumor cells occurs, and these become distributed in the portal venous blood, in the peripheral blood, in the bone marrow, in the wound blood, but above all within the peritoneal cavity. In tumor biology, the dissemination of cells into the systemic blood circulation is to be rated differently to the dissemination into the free abdominal cavity. Detection of individual tumor cells in the blood was already conducted in the 1950s and 1960s, but without it being possible to present a clear relationship to the prognosis.

Even with modern immunocytochemistry and molecular biology methods there has a yet been no success in correlating the detection of systemically disseminated individual tumor cells, as indicators of a minimal residual tumor disease, unambiguously with the actual clinical prognosis of the patient at a convincing level of evidence and of defining this clearly as the prognosis.

The situation changes, however, when various body compartments, such as, for example, the bone marrow, are considered. There is evidence that tumor cells which have been detected in the bone marrow are already located interstitially and have therefore already successfully taken the first steps in extravasation and invasion of the mesenchymal matrix. For mammary carcinoma at least, it has been possible to demonstrate a prognosis association between detection of tumor cells in the bone marrow compartment and the occurrence of skeletal metastases, including the long-term prognosis.

The situation changes when individual tumor cells are found intraperitoneally in the free abdominal cavity. A cytological or even immunocytological detection of tumor cells intraperitoneally in cases of tumors of the gastrointestinal tract, such as gastric carcinoma and colorectal carcinoma, are clear risk indicators for the occurrence of a peritoneal carcinosis. This intraperitoneal tumor dissemination occurs all the more frequently the more pronounced the depth of infiltration of the carcinoma, in particular into the serosa. In macroscopic diagnosis of an attack on the serosa, positive detections of tumor cells were found with a very high probability in accompanying cytological investigations.

During tumor operations an additional aggravating factor is that by exposure of the tissue and manipulation of the tumor-bearing organ, an additional tumor dissemination occurs. The question is raised here as to how the risk of such tumor dissemination can be eliminated intraoperatively. Corresponding experiments with an intraoperative chemoperfusion have so far been less successful, and are also prohibitive for widespread use because of the complexity of the method and the risk. There is also the disadvantage of only being able to reach proliferating tumor cells.

WO 02/20039, WO 00/18806 and WO 2007/093630 disclose trifunctional antibodies which are employed for destruction of tumor cells. WO 02/20039 discloses bispecific and trispecific antibodies which are applied intraperitoneally for treatment of malignant ascites and pleural effusion. However, the antibodies are not administered intraoperatively, in particular not intraoperatively directly into the abdominal cavity, but are applied to patients intraperitoneally via a syringe. The stresses on the human body associated with an operation (activation of the immune system) do not arise in connection with this application.

WO 2004/014421 discloses the use of an antibody-containing preparation which is directed against a tumor-associated antigen, for example against EpCAM, for intraoperative treatment of tumor patients to prevent the dissemination of tumor cells in the context of surgical interventions. According to claim 10, this medicament is applied locally to the tumor tissue and/or to the wound region.

It is therefore an object of the invention to provide a pharmaceutical composition which is suitable for destruction of tumor cells which either have detached themselves, i.e. disseminated, from the tumor, e.g. from the primary tumor or its metastases, without the action of a third party, e.g. by a surgical intervention, and are distributed in the abdominal cavity or in the abdominal space, or are disseminated in the abdominal space or in the abdominal cavity by a surgical intervention for tumor resection, in order to reduce the risk of recurrence by this means.

This object is achieved according to the invention by the preparation of a pharmaceutical composition which, in addition to conventional carrier and/or auxiliary substances, contains a trifunctional bispecific and/or trispecific antibody with the following properties:
(a) binds to a T cell;
(b) binds to at least one tumor-associated antigen which is expressed on intraperitoneally occurring tumor cells;
(c) binds by its Fc part (in the case of trifunctional bispecific antibodies) or by a third specificity (in the case of trispecific antibodies) to Fc receptor-positive cells. Preferred embodiments of these antibodies are described in more detail in the following. The intraoperative application described in more detail in the following is an integral constituent of the solution according to the invention to the problem. The application is carried out in an amount of 1-400 µg.

According to the invention, this composition is applied intraoperatively. In a particularly preferred embodiment, application takes place locally directly into the abdominal cavity, i.e. into the abdominal space. A destruction of e.g. tumor cells disseminated due to the surgical intervention on resection of the primary and/or secondary tumor and which would otherwise be distributed into the patient's body via the body fluids and would significantly increase the probability of renewed tumor growth, i.e. tumor metastases, is achieved by this means. The same therapeutic or prophylactic use is carried out to destroy tumor cells which have detached themselves from the primary or secondary tumor without surgical intervention, that is to say the trifunctional and/or trispecific antibodies employed according to the invention are applied intraoperatively, in a preferred embodiment of the invention directly locally, into the abdominal cavity, and in particular in combination with a surgical intervention which serves to remove the primary and/or secondary tumor.

The application according to the invention for destruction of e.g. tumor cells which have disseminated intraperitoneally due to a surgical intervention and for prophylaxis and therapy of tumor recurrences caused by intraperitoneally disseminated tumor cells, regardless of whether these have been caused by a surgical intervention, always takes place, however, in combination with an application of the antibodies during an operation carried out for removal of the primary tumor or of tumor metastases.

This method of application directly after a tumor resection, that is to say intraoperatively, preferably directly and locally, has the great advantage that the target cells of the trifunctional bispecific or trispecific antibodies, namely the freely disseminated tumor cells in the abdominal cavity, can be easily reached. It is known that disseminated tumor cells already settle on the peritoneal surface and build up a first primitive tumor stroma from fibrin and intercellular matrix within 12-24 hours. A further advantage of the use of the trifunctional bispecific and/or trispecific antibodies according to the invention lies in the prophylaxis of e.g. tumor recurrences caused by tumor cells disseminated intraperitoneally due to the surgical intervention.

It is therefore necessary to reach these tumor cells by means of the pharmaceutical composition before this period of 12-24 hours, since due to the re-settling of the tumor cells and the construction of tumor stroma, they become more difficult for the antibodies to reach. The solution found according to the invention of employing the trifunctional bispecific and/or trispecific antibodies described here intraoperatively after tumor resection, preferably directly locally in the abdominal cavity, forms the decisive novel approach to a successful perioperative tumor therapy, in particular to the prophylaxis of tumor recurrences, in particular peritoneal carcinomatoses, by destruction of freely disseminated tumor cells in the abdominal cavity.

Peritoneal carcinomatosis is a tumor disease in which conventional therapy forms, such as chemotherapy, radiotherapy or surgical methods, usually have not led to satisfactory clinical results. The prognosis for patients with a peritoneal carcinomatosis is therefore also extremely unfavourable, with average survival rates of 3-6 months, depending on the nature of the primary tumor. One of the main factors in the development of peritoneal carcinomatosis is the intraperitoneal dissemination of tumor cells which is described above, caused in particular by the surgical treatment of the tumor, that is to say a tumor resection, but also by penetration of the tumor or by a serous infiltration of the tumor. Persistent intraperitoneal tumor cells embedded in the peritoneum by adhesion molecules and fibrin layers can develop to a macroscopically visible peritoneal carcinomatosis. Studies currently available show that in 100% of the patients affected the persistence of intraabdominal tumor cells leads to development of peritoneal carcinomatosis. This is of particular interest in patients with surgical resection of the primary tumor or a tumor recurrence, and leads to an increased risk of the occurrence of intraabdominal tumor cells. The only possibility of preventing peritoneal carcinomatosis lies in the destruction of persistent intraabdominal tumor cells. According to the invention, it has been found, surprisingly, that the trifunctional bispecific and trispecific antibodies described here, which are known per se, can efficiently destroy disseminated tumor cells on intraoperative application directly after resection of the tumor and can prevent the development of peritoneal carcinomatosis.

A further reason for the route taken according to the invention of intraoperative administration of the trifunctional antibody lies in the postoperative formation of intraabdominal fibrin plaques and adhesions, which cover the disseminated tumor cells and would therefore impede the efficacy of an antibody treatment. An intraoperative administration of the antibodies, preferably in combination with a prompt additional administration of the trifunctional antibody after the resection, renders possible an optimum distribution of the antibody in the peritoneal cavity.

The trifunctional bispecific and trispecific antibodies employed according to the invention are known per se and are described in more detail in the following. These trifunctional antibodies have also already been described for use for destruction of tumor cells. However, it is novel and surprising that during a surgical intervention, after the tumor resection in the abdominal cavity these antibodies are also successfully applied preferably directly at the site of the operation, i.e. locally into the abdominal cavity, in order to destroy there intraperitoneally disseminated tumor cells which, for example, were detached from the tumor body by the intervention or were already present there due to dissemination from the tumor, and thus to prevent them from spreading in the body and the formation of tumor recurrences. According to the invention, the trifunctional antibodies are thus employed for the prophylaxis and therapy of tumor recurrences which are caused in particular due to the surgical intervention and the tumor cells which have thereby disseminated, and in particular during the operation phase, as long as the abdominal cavity is open and has not yet been closed. However, the method of application described according to the invention can also be employed successfully for destruction of tumor cells which have detached themselves from the tumor "independently", without an external influence, and are in the abdominal cavity. In one embodiment of the invention, the antibodies are supplied not directly locally, but systemically; however, it is always decisive that the application takes place during the operation phase, that is to say intraoperatively, that is to say in a phase during which the patient is in an immunosuppressive situation. The administration of antibodies during the operation was hitherto contraindicated for the reasons of immunosuppression described here.

According to the prior art, it was not usual to apply antibodies intraoperatively, e.g. directly locally into the abdominal cavity, in order to destroy tumor cells. The reason lies in an immunosuppressive situation associated with the surgical intervention, which is described in more detail in the following.

Due to the local tissue damage caused during an operation, an acute inflammation reaction is triggered, which comprises the activation of a series of protein cascades, such as e.g. the complement system, coagulation, fibrinolysis and the kinin-kallikrein system. Vasodilation, increased capillary permeability and the loss of immunoglobulins, complement and other proteins in the tissue occur. Furthermore, a number of local mediators are released, e.g. cytokines and eicosanoids, which influence the various processes controlled by hormones. It is presumed that this stress response and the complications associated with it have an adverse effect on the survival rate of the patient precisely in high risk patients, such as tumor patients, in that they interfere e.g. with the immune system. Postoperative infections and an increased risk of metastases due to tumor cells carried along perioperatively, that is to say the intraperitoneally disseminated tumor cells, have an effect on postoperative morbidity and mortality.

Opening up the abdominal cavity, i.e. laparotomy, with subsequent tumor resection by conventional operating techniques lead to an endocrine stress response and perioperative immunosuppression. Leukocytosis with an increased neutrophile and monocyte content and decreased eosinophile and lymphocyte content is typical of operations. The acute phase proteins are increased, the complement components are decreased and their cleavage products are in turn increased.

In cell-mediated immunity, above all the absolute number of lymphocytes is lowered after major interventions, such as laparotomy, and reaches its starting values again postoperatively only after some days. The number of B and T lymphocytes drops and their ratio changes in favour of the B cells. A reduced T cell proliferation, accompanied by various lymphokine changes, leads, as described above, to an increased risk of infection, and increased mortality rate etc.

In humoral immunity, the number of B lymphocytes also drops, and their proliferation response is suppressed.

Numerous studies have shown a depression in cell-mediated immunity in the peri- and postoperative phase, combined with a reduction in the cell count of circulating lymphocytes and natural killer cells, impairment of the activity of natural killer cells, depression of T cell proliferation and reduced neutrophile function. A significant peri- and postoperative lymphopenia results, both the B and the T lymphocytes being affected.

The immunosuppression caused by major surgical interventions which is presented above, described for example by Bettina Gräte in her dissertation, 2004 from the Münster University Hospital, would actually have to have led to the trifunctional bispecific and trispecific antibodies according to the invention being unable to display their activity. In fact, these trifunctional antibodies not only have the capacity for direct destruction of the tumor cells, but are also capable of inducing an immunity directed against the tumor to be treated. By their binding to the Fc receptor, they are capable of activating an Fc receptor-positive cell and by this means of initiating or increasing the expression of cytokines and/or of costimulatory antigens. These cytokines and costimulatory antigens transmit to the T cell at least a second activation signal required for physiological activation of the T cell, and therefore increase the expression of activation markers, promote proliferation of T cells and destroy the tumor cell.

The trifunctional antibodies administered according to the invention have two, different binding arms and can therefore recognise and bind two different antigen structures simultaneously. With one binding arm the trifunctional antibody binds to a tumor antigen on the tumor cell, and with the aid of the second antigen structure it binds to T lymphocytes and guides the two into a close spatial context, so that the T cell is put in the position to destroy the tumor cell.

It was to be assumed that this highly complex immune response leading to stimulation of the immune systems against the tumor and to a direct destruction of the tumor cell was not active on intraoperative administration, preferably with a direct administration intraoperatively directly locally into the abdominal cavity, and indeed because of the immunosuppressive action described above, in which the patient's body is caused by the operation to compensate the "excessive" immune response due to the abdominal surgical intervention. The body in fact attempt to repress specific cell immune functions, for example the activity of phagocytes in the abdominal cavity.

The body furthermore attempts, by immunosuppression, to reduce the increased formation of cytokines and acute phase proteins, in order to bring the body back into a normal, physiological immune situation. It was to be expected from this postoperative suppression of the immune system that the administration of the trifunctional antibodies (trAb) does not lead to a destruction of intraperitoneally disseminated tumor cells. For this reason antibodies also have not hitherto been used locally intraoperatively, since success was not foreseeable. Completely surprisingly, it has been found, however, that the trifunctional bispecific and trispecific antibodies chosen according to the invention are most certainly capable, in spite of the immunosuppressive situation, of making use of their immunological function and of causing direct destruction of the tumor cells. These functions are, in particular, a physiological activation of the T cells, which is achieved by costimulatory signals mediated to the T cells by the activated accessory cells. Furthermore, in addition to the T cells, accessory cells are recruited, so that further killer mechanisms are initiated, such as e.g. phagocytosis. By these mechanisms, the trifunctional antibodies are capable of also destroying tumor cells which are resistant to T cells. This destruction of disseminated tumor cells takes place in spite of the immunosuppressive situation described, following tumor resection in the abdominal cavity.

The use claimed according to the invention and the purpose-oriented pharmaceutical composition claimed according to the invention and the healing method claimed according to the invention are described in more detail in the following with reference to claim 1. Preferred embodiments of the invention emerge from the sub-claims, the present description and the embodiment examples.

The trifunctional bispecific and trispecific antibodies included in the invention are employed during surgical intervention in the abdominal cavity. The abdominal cavity is first opened, i.e. a laparotomy is performed, with subsequent tumor resection by operating techniques known per se. The trifunctional bispecific and trispecific antibodies are thus employed intraoperatively, i.e. during a surgical intervention or during an operation. In a particularly preferred embodiment of the invention, the antibodies are applied by direct application into the abdominal cavity after the resection of the tumor material, but at any rate before closing of the abdominal cavity. The expressions "abdominal space" and "abdominal cavity" are used synonymously here. The core of the invention thus lies in the direct contact between the trifunctional bispecific and trispecific antibody, such as is described in the present application, and the environment of the abdominal cavity, and not in administering the antibody postoperatively. Only in a preferred embodiment of the invention is at least one further second, third etc. antibody dose administered additionally after the surgical intervention, i.e. after closure of the abdominal space, in order to destroy any remaining tumor cells which have not yet been destroyed.

The tumors are tumors which conventionally attack organs in the abdominal space. These are, in particular, gastrointestinal tumors, e.g. tumors of the stomach, the small and large intestine, the liver, the kidneys, the ovary, the pancreas, the appendix and the pseudomyxoma. After removal of the tumor, the trifunctional bispecific antibody or the trispecific antibody or a mixture of the two antibodies is applied into the abdominal cavity. Since the antibody is as far as possible to come into contact with all the surfaces in the abdominal cavity as completely as possible, that is to say not only with the wound region and the tumor tissue, it is applied in a physiologically acceptable medium which is suitable for irrigation of the abdominal cavity. Such a medium is preferably an isotonic or physiological solution, preferably an isotonic or physiological saline solution. All other media which are suitable for uptake and for distribution of the antibody in the abdominal cavity and are physiologically acceptable can of course likewise be employed, for example buffer solutions.

Further pharmaceutically active substances can also be added to the medium, for example antibiotics, antimycotics, antivirus agents, agents having an antiinflammatory action, agents having an analgesic or antipyretic action, further antitumor agents, such as cytostatics, or other antibodies etc. The additional administration of non-specific immunomodulators, such as GM-CSF, G-CSF etc., is also possible. It is left to the person skilled in the art to decide on the further pharmaceutically active substances which are added to the irrigation liquid. The person skilled in the art will make a decision on the nature and the amount of these further active compounds in association with the disease to be treated. Pharmaceutically inactive substances can additionally be added, e.g. stabilising agents, such as polysorbates, preservatives etc.

The medium containing the antibody will remain in the abdominal cavity in a direct local application form for a period of time sufficient to establish complete contact between the antibody and the disseminated tumor cells. This period of time will be determined by the doctor conducting the treatment, who will make his decision according to the disease to be treated, the condition of the patient and further parameters. The medium containing the antibody preferably remains in the abdominal cavity for a period of time of several minutes, e.g. 1-10 minutes or 1-5 minutes, or up to one hour, possibly even longer. The liquid particularly preferably remains in the abdominal cavity, it then preferably being present in an amount such that it can be absorbed by the body. Liquids are conventionally largely absorbed by the body in the abdominal space at the latest after 24 hours. Preferably, the liquid is thus employed, i.e. applied intraperitoneally, that is to say into the abdominal cavity, in an amount such that it can be absorbed by the body.

In a preferred embodiment of the invention, the abdominal cavity is brought into contact with the physiologically acceptable medium containing the antibody, that is to say the antibody is applied into the abdominal cavity in a physiologically acceptable medium, at least once. The introduction takes place, for example, by means of a syringe into the open abdominal space (i.e. not through the closed abdominal wall), by pouring in, or by other methods of application known per se. In one embodiment of the invention, the antibody is employed in the form of an irrigation liquid in order to discharge the disseminated tumor cells by the irrigation itself and the subsequent removal of the irrigation liquid. This irrigation can preferably be repeated once or twice. Preferably, however, an amount of liquid acceptable for the patient remains in the abdominal cavity after application, in order to render possible sufficiently long contact between the antibody and the disseminated tumor cells and in order to allow all the surfaces of the abdominal space to come into contact with the antibodies as completely as possible. As described above, the physiologically acceptable medium with the antibody is absorbed by the body. Alternatively, it can also be actively removed.

The physiologically acceptable medium can be applied into the abdominal cavity in any desired manner determined by the doctor. Examples of this are direct pouring in of the medium, application via a catheter or via an indwelling catheter or via hose systems. Further preferred embodiments are percutaneously inserted catheters or subcutaneously implanted port systems.

The amount of antibody to be applied is in turn determined by the doctor conducting treatment, according to the disease to be treated. The antibody is administered in an amount of 1-400 µg per application, a maximum of 500 µg, preferably in an amount of 5-100 µg, furthermore preferably in an amount of 10-20 µg. Further amounts which can be employed are 10-50 µg, 20-80 µg and 30-60 µg. The dose amounts of antibody administered can also be chosen variably. It goes without saying for a person skilled in the art that these amounts data are guideline values which can be entirely different from patient to patient, from disease to disease and from antibody to antibody. It belongs to the technical knowledge of the medical specialist to choose the amount of antibody to be individually employed accordingly, for example as a function of how the patient reacts to the antibody application.

According to the invention, application of the antibodies thus takes place during the immunosuppressive situation caused by the surgical intervention and therefore differs significantly from a conventional method of application in the prior art, in which the antibodies can indeed be applied to the patient directly into the abdominal cavity, but no immunosuppressive environment exists, since the use is not intraoperative and the abdominal space also is not open.

In a further embodiment of the invention, the antibody is administered postoperatively, preferably in at least one further dose, for example in the form of a second dose for activation and proliferation of the immune cells and preferably at least in a third dose for destruction of remaining residual and disseminated tumor cells. The number of further applications depends, for example, on the reaction of the patient to the application of antibodies, for example on the side effects, and is determined by the doctor conducting the treatment. Preferred amounts of the antibody to be applied are likewise determined by the doctor conducting treatment, according to the disease to be treated and the antibody. As guideline values, an amount of 1-20 µg, preferably 5-10 µg can be administered postoperatively as the second dose, a subsequent dose preferably in an amount of 20-100 µg, preferably 30-60 µg, and further subsequent administrations preferably in an amount of 100-500 µg, preferably 100-300 µg. The postoperative application can take place either intraperitoneally or intravenously, or via another method of application known per se.

In a further embodiment of the invention, the antibody is administered postoperatively in an amount of 5-1,000 µg, preferably 10-500 µg, furthermore preferably 10-150 µg.

The administration preferably takes place intraperitoneally, postoperative administration taking place, for example, 2 to 5 times.

The administration takes place at intervals of time, 48-72 hours after the operation e.g. being chosen. For example, a period of time of 2-3 days plus/minus several hours between the individual applications is chosen. The applications are preferably continued postoperatively over a period of time of 12-20 days. If e.g. murine antibodies according to the invention are used, for example, the HAMA (human anti-mouse antibody) reaction is determined, which in general starts after 16-21 days, in some patients earlier, in others later or not at all. However, even the start of an HAMA reaction does not necessarily influence the activity during this period of time, since under certain circumstances no adequate HAMA level are yet reached here. Experience to date shows that high HAMA levels can also entirely be tolerated without relevant side effects or a significant weakening of the effectiveness of the trifunctional antibodies employed according to the invention having been observed.

The trifunctional bispecific and/or trispecific antibodies employed according to the invention are known per se. They are antibodies with the following properties:
  (a) binds to a T cell;
  (b) binds to at least one tumor-associated antigen which is expressed on intraperitoneally occurring tumor cells;
  (c) binds by its Fc part (in the case of trifunctional bispecific antibodies) or by a third specificity (in the case of trispecific antibodies) to Fc receptor-positive cells.

The antibodies are so-called intact trifunctional bispecific and trispecific antibodies. By the treatment, not only is the surprising direct destruction of the tumor cells, which is described above, on intraoperative application during the immunosuppressive phase achieved, but in particular an immunity directed against the tumor to be treated can be induced by the subsequent administrations.

"Intact antibodies" are to be understood as meaning those which have a functional Fc part. These are preferably heterologous antibodies, i.e. they are composed of heavy immunoglobulin chains of different sub-classes (combinations, also fragments) and/or origin (species).

In addition to features a, b and c described above, in preferred embodiments of the invention the antibodies employed also have the further features d) and e):

d) activates the Fc receptor-positive cell by its binding to the Fc receptor-positive cell, as a result of which the expression of cytokines and/or of costimulatory antigens is initiated or increased;

e) the costimulatory antigens and/or cytokines transmit to the T cell at least a 2nd activation signal required for physiological activation of the T cell, this activation manifests itself in the upwards regulation of activation markers, the destruction of the tumor cell and/or in a proliferation of the T cell.

The invention is described in the following in particular by the example of trifunctional bispecific antibodies. However, the results can also be achieved with trispecific antibodies.

The antibodies which can be used according to the invention are capable of activating the Fc receptor-positive cell, as a result of which the expression of cytokines and/or costimulatory antigens is initiated or increased.

In the case of trispecific antibodies, binding to the Fc receptor-positive cells preferably takes place, for example, via the Fc receptor of Fc receptor-positive cells or also via other antigens on Fc receptor-positive cells (antigen-presenting cells), such as e.g. the mannose receptor.

The heterologous bispecific and/or trispecific antibodies which can be used according to the invention are known per se. They are described, for example, in Lindhofer et al., Blood, 88:4651, 1996 or Lindhofer et al., J. Immunology, 155:219, 1995.

An upwards regulation of MHC 1 and an activation of the intracellular processing machinery (proteasome complex) takes place on the tumor cell due to the release of cytokines (such as e.g. INF-γ and TNF-α) in the immediate neighbourhood of the tumor cell. The cytokines are released due to trifunctional antibody-mediated activation of T cells and accessory cells. That is to say by the intact bsAb, not only are tumor cells destroyed or phagocytised, but their tumor immunogenicity is also increased indirectly.

The activation of the Fc receptor-positive cell by the trAb depends on the sub-class or sub-class combination of the trAb. As has been demonstrated in in vitro studies, for example, trAb of the sub-class combination mouse IgG2a/rat IgG2b are capable of binding to Fc receptor-positive cells and of simultaneously activating these, which leads to upwards regulation or new formation (expression) of costimulatory antigens, such as e.g. CD40, CD80 or CD86, on the cell surface of these cells (Zeidler et al., J. Immunol., 163:1246, 1999). On the other hand, bsAb of the sub-class combination mouse IgG1/rat IgG2b are indeed capable of binding to Fc receptor-positive cells (Haagen et al., J. Immunology, 1995, 154: 1852-1860), but evidently cannot active these to a comparable extent (Gast et al., Cancer Immunol. Immuntherap., 1995, 40: 390).

While the intact trAb binds and simultaneously activates the T cell with one binding arm (e.g. on CD3 or CD2), costimulatory signals can be transmitted to the cell from the Fc receptor-positive cell bound to the Fc part of the trAb. That is to say only the combination of activation of the T cell via one binding arm of the trAb and simultaneous transmission of costimulatory signal from the Fc receptor-positive cell to the T cell leads to an efficient T cell activation. Tumor-specific T cells which have bee inadequately activated on the tumor cell and are anergic can likewise be reactivated after the treatment according to the invention with intact bispecific antibodies or trispecific antibodies.

A further important aspect is the possible phagocytosis, processing and presentation of tumor constituents by the accessory cells (monocytes/macrophages, or dendritic cells) brought forward and activated by the trAb. Both tumor-specific CD4- and CD8-positive cells can be generated by this conventional mechanism of presentation of antigens. Tumor-specific CD4 cells moreover play an important role for the induction of a humoral immune response in connection with T-B cell cooperation.

Trifunctional and trispecific antibodies can bind with one binding arm to the T cell receptor complex of the T cell and with the second binding arm to tumor-associated antigens on the tumor cell. They thereby activate T cells, which destroy the tumor cells by release of cytokines or apoptosis-mediating mechanisms. There is moreover evidently the possibility that in the context of activation with bispecific antibodies, T cells recognise tumor-specific antigens via their receptor and as a result a permanent immunisation is initiated. In this context, the intact Fc part of the trifunctional or trispecific antibody which mediates the binding to accessory cells, such as e.g. monocytes/macrophages and dendritic cells, and prompts these themselves to become cytotoxic and/or to transmit simultaneously important costimulatory signals to the T cell is of particular importance. A T cell response under certain circumstances also against hitherto unknown tumor-specific peptides can evidently be induced in this manner.

By redirection of under certain circumstances anergised, tumor-specific T cells to tumor cells by means of trifunctional and/or trispecific antibodies with simultaneous costimulation of such T cells by accessory cells which bind to the Fc part of the trifunctional or trispecific antibody, the anergy of cytotoxic T cells (CTLs) could be eliminated. That is to say a T cell tolerance existing to the tumor in the patient can be broken by means of intact heterologous trifunctional and/or trispecific antibodies and a permanent tumor immunity can thus be induced.

The antibodies employed according to the invention are preferably capable of reactivation of tumor-specific T cells in anergy. They are furthermore capable of induction of tumor-reactive complement-binding antibodies and therefore of induction of a humoral immune response.

Binding is preferably via CD3, CD2, CD4, CD5, CD6, CD8, CD28, CD40L and/or CD44 on the T cell. The Fe receptor-positive cells have at least one type I or II Fcγ receptor.

Antibodies which can be employed according to the invention are capable of binding to monocytes, macrophages, dendritic cells, "natural killer" cells (NK cells) and/or activated neutrophilic cells as Feγ receptor I and/or III-positive cells (Zeidler, 1999, Zeidler 2000 loc. cit.).

The antibodies which can be employed according to the invention have the effect that the expression of CD40, CD80, CD86, ICAM-1 and/or LFA-3 as costimulatory antigens and/or the secretion of cytokines is initiated or increased by the Fc receptor-positive cell. The cytokines are preferably IL-1, IL-2, IL-4, IL-6, IL-8, IL-12, INF-γ and/or TNF-α.

The trifunctional bispecific antibodies which can be employed according to the invention are, for example:
an anti-CD3 X anti-tumor-associated antigen and/or anti-CD4 X anti-tumor-associated antigen and/or anti-CD5

X anti-tumor-associated antigen and/or anti-CD6 X anti-tumor-associated antigen and/or anti-CD8 X anti-tumor-associated antigen and/or anti-CD2 X anti-tumor-associated antigen and/or anti-CD28 X anti-tumor-associated antigen and/or anti-CD40L X anti-tumor-associated antigen antibody and/or anti-CD44 X anti-tumor-associated antigen antibody The trispecific antibodies which can be employed according to the invention are preferably:

an anti-CD3 X anti-tumor-associated antigen and/or anti-CD4 X anti-tumor-associated antigen and/or anti-CD5 X anti-tumor-associated antigen and/or anti-CD6 X anti-tumor-associated antigen and/or anti-CD8 X anti-tumor-associated antigen and/or anti-CD2 X anti-tumor-associated antigen and/or anti-CD28 X anti-tumor-associated antigen and/or anti-CD40L X anti-tumor-associated antigen antibody and/or anti-CD44 X anti-tumor-associated antigen antibody A trispecific antibody which binds to Fc receptors with its 3rd specificity initiates the same immunological mechanisms as a trifunctional bispecific antibody with an intact Fc part. Like a bispecific trifunctional antibody, a trispecific antibody also induces expression of cytokines and/or costimulatory antigens, which in turn leads to a stimulation of the bound T cell.

There are reports in the literature which in fact describe the abovementioned properties likewise for Fc receptor-binding antibodies. Thus, Weiner et al. report (Cancer Res. 55:4586, 1995) that after administration of an anti-Her2 X anti CD 16 bispecific antibody, a 100-fold increase in the cytokines TNF-alpha, IL-6 and IL-8 and, in attenuated form, an increase in GM-CSF and interferon-gamma was observed. CD16 is another name for the type III Fc-gamma receptor.

Similar results are reported by Pullarkat et al., (Cancer Immunol. Immunother. 48:9, 1999). Here, an increase in the cytokines IL-6, G-CSF and TNF-alpha was measured in patients after treatment with a bispecific antibody anti-Her2 X anti-CD64 (corresponds to type I Fc-gamma receptor).

It can be concluded inasmuch from these reports that antibodies which are directed against Fc receptors are also entirely capable of directly activating Fc receptor-positive cells via binding, which manifests itself in the release e.g. of certain cytokines.

Ely et al. (Blood, 87:3813, 1996) or Wahl et al. (Clin. Cancer Res. 9:4240, 2003) e.g. furthermore show that a phagocytosis can also be initiated by anti-Fc receptor antibodies.

The ability to prepare trispecific antibodies with the properties of claim 1 thereby exists, and is described in more detail on the following pages.

The antibodies which can be employed according to the invention recognise and bind tumor-associated antigens which are known per se and typically occur on tumor cells in the abdominal space. Tumor-associated antigens on a tumor cell which belong to the following groups are preferably recognised by the antibodies. Her2/neu, CD20, CD30 EpCAM, G250, proteoglycans, GD2, GD3, MHC II, EGF-R, CA125 and CEA.

The antibody is preferably the following antibodies: an anti-Her2/neu x anti-CD3 antibody or an anti-EpCAM x anti-CD3 antibody which binds to type I/III Fc-γ receptors, in each case preferably with the isotype combination rat IgG2b/mouse IgG2a or mouse [VH-CH1, VL-CL]-human IgG1-[hinge]-human IgG3 [Caucasian allotypes G3m(b+g)=no binding to protein A]-[CH2-CH3]/rat [VH-CH1, VL-CL]-human IgG1-[hinge]-human IgG1-[CH2-CH3].

The trispecific antibodies which can be employed according to the invention have at least a T cell-binding arm, a tumor cell-binding arm and a binding arm which binds to Fc receptor-positive cells. This last-mentioned binding arm can be an anti-Fc receptor-binding arm or a mannose receptor-binding arm.

The trifunctional antibody is preferably a heterologous intact rat/mouse bispecific antibody.

T cells are activated and redirected towards the tumor cells with the trifunctional and trispecific antibodies which can be employed according to the invention. Heterologous intact bispecific antibodies which can preferably be employed are chosen from one or more of the following isotype combinations:

rat IgG2b/mouse IgG2a,
rat IgG2b/mouse IgG2b,
rat IgG2b/mouse IgG3,
rat IgG2b/human IgG1,
rat IgG2b/human IgG2,
rat IgG2b/human IgG3 [oriental allotype G3m(st)=binding to protein A],
rat IgG2b/human IgG4,
rat IgG2b/rat IgG2c,
mouse IgG2a/human IgG3 [Caucasian allotypes G3m(b+g)=no binding to protein A, labelled with * in the following]
mouse IgG2a/mouse [VH-CH1, VL-CL]-human IgG1-[hinge]-human IgG3*-[CH2-CH3]
mouse IgG2a/rat [VH-CH1,VL-CL]-human IgG1-[hinge]-human IgG3*-[CH2-CH3]
mouse IgG2a/human [VH-CH1,VL-CL]-human IgG1-[hinge]-human IgG3*-[CH2-CH3]
mouse [VH-CH1,VL-CL]-human IgG1/rat [VH-CH1,VL-CL]-human IgG1-[hinge]-human IgG3*-[CH2-CH3]
mouse [VH-CH1,VL-CL]-human IgG4/rat [VH-CH1,VL-CL]-human IgG4-[hinge]-human IgG4[N-terminal region von CH2]-human IgG3*[C-terminal region von CH2: >AA position 251]-human IgG3*[CH3]
rat IgG2b/mouse [VH-CH1,VL-CL]-human IgG1-[hinge-CH2-CH3]
rat IgG2b/mouse [VH-CH1,VL-CL]-human IgG2-[hinge-CH2-CH3]
rat IgG2b/mouse [VH-CH1,VL-CL]-human IgG3-[hinge-CH2-CH3, oriental allotype]
rat IgG2b/mouse [VH-CH1,VL-CL]-human IgG4-[hinge-CH2-CH3]
human IgG1/human [VH-CH1,VL-CL]-human IgG1-[hinge]-human IgG3*-[CH2-CH3]
human IgG1/rat [VH-CH1,VL-CL]-human IgG1-[hinge]-human IgG4[N-terminal region of CH2]-human IgG3*[C-terminal region of CH2: >AA position 251]-human IgG3*[CH3]
human IgG1/mouse [VH-CH1,VL-CL]-human IgG1-[hinge]-human IgG4 [N-terminal region of CH2]-human IgG3*[C-terminal region of CH2: >AA position 251]-human IgG3*[CH3]
human IgG1/rat [VH-CH1,VL-CL]-human IgG1-[hinge]-human IgG2[N-terminal region of CH2]-human IgG3*[C-terminal region of CH2: >AA position 251]-human IgG3*[CH3]
human IgG1/mouse [VH-CH1,VL-CL]-human IgG1-[hinge]-human IgG2[N-terminal region of CH2]-human IgG3*[C-terminal region of CH2: >AA position 251]-human IgG3*[CH3]
human IgG1/rat [VH-CH1,VL-CL]-human IgG1-[hinge]-human IgG3*-[CH2-CH3]

human IgG1/mouse [VH-CH1,VL-CL]-human IgG1-[hinge]-human IgG3*-[CH2-CH3]

human IgG2/human [VH-CH1,VL-CL]-human IgG2-[hinge]-human IgG3*-[CH2-CH3]

human IgG4/human [VH-CH1,VL-CL]-human IgG4-[hinge]-human IgG3*-[CH2-CH3]

human IgG4/human [VH-CH1,VL-CL]-human IgG4-[hinge]-human IgG4[N-terminal region of CH2]-human IgG3*[C-terminal region of CH2: >AA position 251]-human IgG3*[CH3]

mouse IgG2b/rat [VH-CH1,VL-CL]-human IgG1-[hinge]-human IgG3*-[CH2-CH3]

mouse IgG2b/human [VH-CH1,VL-CL]-human IgG1-[hinge]-human IgG3*-[CH2-CH3]

mouse IgG2b/mouse [VH-CH1,VL-CL]-human IgG1-[hinge]-human IgG3*-[CH2-CH3]

mouse [VH-CH1,VL-CL]-human IgG4/rat [VH-CH1,VL-CL]-human IgG4-[hinge]-human IgG4-[CH2]-human IgG3*-[CH3]

human IgG1/rat [VH-CH1,VL-CL]-human IgG1[hinge]-human IgG4-[CH2]-human IgG3*[CH3]

human IgG 1/mouse [VH-CH1,VL-CL]-human IgG1 [hinge]-human IgG4-[CH2]-human IgG3*[CH3]

human IgG4/human[VH-CH1,VL-CL]-human IgG4-[hinge]-human IgG4-[CH2]-human IgG3*-[CH3]

The antibodies which can be used according to the invention are preferably monoclonal, chimaeric, recombinant, synthetic, semisynthetic or chemically modified intact or non-intact antibodies with, for example, Fv, Fab, scFv or F(ab)$_2$ fragments.

Antibodies or derivatives or fragments from humans are preferably used, or those which are modified such that they are suitable for use in humans (so-called "humanised antibodies") (see e.g. Shalaby et al., J. Exp. Med. 175 (1992), 217; Mocikat et al., Transplantation 57 (1994), 405) are preferred.

The preparation of the various abovementioned antibody types and fragments is familiar to the person skilled in the art. The preparation of monoclonal antibodies, which preferably have their origin in mammals, e.g. human, rat, mouse, rabbit, goat or cameline species, can be carried out by means of conventional methods, such as are described e.g. in Köhler and Milstein (Nature 256 (1975), 495), in Harlow and Lane (Antibodies, A Laboratory Manual (1988), Cold Spring Harbor) or in Galfré (Meth. Enzymol. 73 (1981), 3) or DE 195 31 346.

It is furthermore possible to prepare the antibodies described by means of recombinant DNA technology by techniques familiar to the person skilled in the art (see Kurucz et al., J. Immunol. 154 (1995), 4576; Holliger et al., Proc. Natl. Acad. Sc. USA 90 (1993), 6444).

The preparation of antibodies with two different specificities, the so-called bispecific antibodies, is possible on the one hand by using recombinant DNA technology, but also by the so-called hybrid hybridoma fusion technique (see e.g. Milstein et al., Nature 305 (1983), 537). In this, hybridoma cell lines which produce antibodies with in each case one of the desired specificities are fused and cell clones (quadromas) which produce antibodies with both specificities are identified and isolated.

The problem on which the invention is based can be solved by both trifunctional bispecific and trispecific antibodies, which preferably have the properties and actions characterised. The preparation of antibodies with two and three specificities is described in more detail in the following. The provision of such trifunctional and trispecific antibodies belongs to the prior art and reference is made here, in the full content, to the literature describing such preparation techniques.

The preparation of antibodies with three specificities, so-called trispecific antibodies, by which the problem on which the invention is based can likewise be solved, can be carried out, for example, by coupling a third antigen binding site with a further specificity, e.g. in the form of a "single chain variable fragment" (scFv), on to one of the heavy Ig chains of a bispecific antibody. The scFv can be bound to one of the heavy chains, for example, via a -S-S(G$_4$S)$_n$D-I linker (S=serine, G=glycine, D=aspartate, I=isoleucine).

Analogously to this, trispecific F(ab)$_2$ constructs can be prepared by replacing the CH2-CH3 regions of the heavy chain of one specificity of a bispecific antibody by an scFv with a third specificity, while the CH2-CH3 regions of the heavy chain of the other specificity are removed, for example, by incorporation of a stop codon (at the end of the "hinge" region) into the coding gene, e.g. by means of homologous recombination.

The preparation of trispecific scFv constructs is also possible. In this, three VH-VL regions which represent three different specificities are arranged one after the other in series.

Intact bispecific antibodies e.g. are used according to the invention. Intact bispecific antibodies are composed of two antibody half molecules (one H and L immunoglobulin chain each) which each represent a specificity, and moreover have, like normal antibodies also, an Fc part with the known effector functions. They are preferably prepared by quadroma technology. This preparation process is described by way of example in DE-A-44 19 399. For complete disclosure, reference is made to this publication in full content also with respect to a definition of bispecific antibodies. Other preparation processes can of course also be employed, as long as they lead to the intact bispecific antibodies of the above definition which are necessary according to the invention.

For example, according to the preparation process of Lindhofer et al., J. Immunology 1995, 155: 219, intact bispecific antibodies are produced in an adequate amount. The combination of 2 bispecific antibodies against 2 different tumor-associated antigens (e.g. c-erb-B2 and EpCAM) on mammary carcinoma cells minimises the risk that tumor cells which express only one antigen remain unrecognised.

Further advantages of intact bsAb with the ability to redirect T cells over the abovementioned bsF(ab')2 fragments are, specifically:

1. An intact trAb can bind Fc receptor-positive cells and contribute on the one hand directly to destruction of the tumor via ADCC (antibody-dependent cell-mediated cytotoxicity) and on the other hand, as stated above in more detail, to T cell activation.
2. By intact T cell-redirecting trAb, anergised tumor-specific T cells which can be reactivated according to the invention directly on the tumor are brought to the tumor cell. This cannot be achieved by a bsF(ab')2 fragment with the specificities of anti-CD64X-anti-tumor-associated antigen.

Binding of the trAb to Fcγ-RI has two essential advantages with respect to an optimum anti-tumor activity:

(1) Fcγ-RI-positive cells have the ability to eliminate tumor cells by means of ADCC and inasmuch can contribute synergistically to the anti-tumor action of the cytotoxic T cells brought to the tumor cell by the trAb.
(2) Fcγ-RI-positive cells (such as e.g. monocytes/macrophages/dendritic cells) are capable of delivering important costimulatory signals, as similarly in the case of antigen presentation, to the T cell and therefore of preventing anergising of the T cell. As a desirable by-product, on the basis of the interaction of T cell with accessory cell and tumor cell mediated by intact trAb, even T cells of which the T cell receptor recognises tumor-specific peptides (presented on the tumor cell via MHC antigens), can furthermore be stimulated. The costimuli necessary for correct activation of the T cell would be delivered in this constellation by the accessory cell (e.g. monocyte). The antibody according to the invention should inasmuch, in addition to the direct T cell receptor-independent, trAb-mediated tumor destruction, likewise activate and generate tumor-specific T cells which continue to patrol in the patient after degradation of the trAb. That is to say, as similarly in gene therapy approaches (e.g. by incorporation of costimulatory antigens, such as B-7, into the tumor cell), the tumor tolerance in the patient can be broken through by means of intact trAb.

The intraoperative application of antibodies to prevent the dissemination of tumor cells is known from WO 2004/014421. It is first to be said that the examples of this application give no indication at all of the activity of the therapy claimed. Example 1 shows the preparation of a Lewis-Y antibody. Under the heading "Use during tumor resection", an intravenous treatment with the antibody-containing preparation "immediately before the operation over a period of time of 2 hours" with a dose of 50 mg is described. "Thereafter, the tumor is removed within 4 hours."

In Example 2, the inhibition of tumor growth by antibodies against Lewis-Y in naked mice is described. Tumor cells are applied into the naked mice, and 21 to 24 hours after the application of the tumor cells a first intraperitoneal injection of the antibody-containing preparation is given.

In Example 4, the antibody-containing preparation is administered intravenously to a patient with pleural effusion a maximum of 24 hours before removal of the effusion.

In none of the three examples of WO 2004/014421 is evidence provided that intraoperative treatment of tumor patients is successful, and in particular the side effects to be expected, which are described in more detail in the following, also do not occur.

The distinction is also to be made according to the invention between the intraoperative application according to the invention directly locally into the abdominal cavity and an application "directly into the wound region", such as is described in WO 2004/014421.

As described in more detail above, small amounts of trifunctional antibodies are employed according to the invention. In contrast, in Example 1 of WO 2004/014421 a dose of 50 mg is administered, in Example 4a dose of 100 mg, and it is proposed according to claim 9 to administer to the patient preferably at least 100 mg, most preferably at least 200 mg and in total up to 2 g systemically in a single dose.

A further important criterion to distinguish from WO 2004/014421 lies in the use according to the invention of trifunctional and trispecific T cell-activating antibodies. As will be described in more detail on the following pages, a high risk was associated with the use of the trifunctional and trispecific antibodies employed according to the invention. The antibodies employed in WO 2004/014421 are merely capable of binding and activating accessory cells. The trifunctional antibodies employed according to the invention are additionally also capable of recruiting and activating T cells. Since T cells in particular have a particularly high risk potential, the assertions put forward in WO 2004/014421, which, as shown above, furthermore are not backed up by any experimental data at all, cannot be applied to the antibodies of the present invention. An example of an excessive immune reaction is given by the antibody TGN1412, with which, on administration in a phase I study, unexpected and serious side effects occurred in the volunteers. In a letter to the editor of the journal Nature Biotechnology (published in Nature Biotechnology, vol. 24, pages 493 to 496, no. 5, May 2006), the Paul-Ehrlich-Institut was prompted to point out the particular risk of T cell-binding antibodies. In particular, trispecific antibodies which have a particularly high risk potential are mentioned.

Summarising, for a person skilled in the art it was not obvious to induce in a patient, in whom, caused by the operation, an acute inflammation reaction was generated, a further activation of the immune system with the administration of trifunctional antibodies. The life-threatening effects of TGN1412 from Tegenero on 13 Mar. 2006 was an argument against the use of bispecific trifunctional antibodies, that is to say trifunctional antibodies which activate the immune system via T cells. Operative abdominal trauma already leads to an inflammatory stimulation of immune cells, in particular intraperitoneally present immune cells at the site of the traumatisation. It is therefore not obvious and in particular cannot be deduced from WO 2004/014421 that no further contraindicated stimulation of the immune system takes place by the application according to the invention of trifunctional antibodies and, although the body subsequently attempts to suppress the immune reaction, nevertheless a positive immune reaction caused by the trifunctional antibodies and a destruction of the tumor cells can be achieved.

The invention is explained in more detail in the following with the aid of embodiment examples which, with the aid of clinical data, already fortunately show the surprisingly positive properties of the use of trifunctional bispecific antibodies. The usefulness of the trispecific antibodies described above is supported by these experiments, which can be applied thereto to the full extent.

1. Embodiment Example

A 59-year old patient was operated on for a pronounced gastric carcinoma. The gastric carcinoma with peritoneal carcinosis had already been diagnosed 2 months beforehand, and chemotherapy (PLF regime) had primarily been undertaken. The patient had now complained increasingly of a pyloric stenosis, so that on the basis of this, palliative gastric resection had been indicated. At the same time it had been discussed whether to already start antibody application intraoperatively in the context of a healing attempt. After complete removal of the stomach with the colon transversum and spleen, intraoperative installation of the antibody was then carried out. For the application, 100 µg of the trifunctional antibody ertumaxomab with the features anti-Her2/neu X anti-CD3 (isotype combination mouse IgG2a x rat IgG2b) were taken up in 500 ml of NaCl solution and the mixture was applied intraperitoneally. An intraabdominal port system had additionally also been implanted, via which antibody had been applied 4× in total from the 11th postoperative day. As an indication of the efficacy of the antibodies, the wound fluid/irrigation liquid was collected after the intraoperative application of antibody and analysed again immunocytochemically for tumor cells. No further indication of tumor cells was found here, so that this can be regarded as evidence of the efficacy of this concept.

In spite of this extremely advanced stage of the tumor, the patient survived the operation for 9 months, which was a very positive result given an average survival time of an expected 3 months. In addition, the patient survived for 6 months without symptoms of a considerable disturbance in passage in the gastrointestinal tract.

2. Embodiment Example

In the second healing attempt, a 35-year old female patient with a very extensive gastric carcinoma was operated on and application of trifunctional antibodies was again carried out intraoperatively directly after resection of the tumor. A diagnostic laparoscopy had been performed on the patient 4 days before the operation for histological confirmation.

Needless to say, the intraoperative lavage directly after the laparotomy showed an abundance of tumor cells, so that it was decided to attempt the antibody application intraoperatively. It had been demonstrated beforehand that the tumor cells express Her2/neu as the target antigen. This extensive operation included a gastrectomy, a hemicolectomy, a splenectomy and cholecystectomy. The intraoperative application of antibodies (10 µg of ertumaxomab) was tolerated by the patient without problems, so that she recovered as expected postoperatively. It was decided to continue the antibody therapy intravenously on the 8th postoperative day. For this, 6 µg of ertumaxomab were applied intravenously, although this had to be discontinued after 2 hours because of a sudden rapid increase in fever.

In spite of discontinuation of the therapy, the patient showed a renewed increase in fever on the following day, so that in further diagnosis pneumonia in the left lower lobe emerged as the cause. This was then treated with antibiotics. The patient was then treated with 10 µg of the antibody ertumaxomab i.p. again for a further 10 days. The course was without problems and the patient coped with it well. 2 days later a further i.p. therapy with the same antibody was increased to 100 µg. This application was also tolerated without problems, so that the patient could be discharged the following day.

The cytological analysis of the wound fluid on the 3rd postoperative day showed a complete depletion of tumor cells, which is rated as an indication of the efficacy of the intraoperative antibody application.

3. Embodiment Example

Experimental Design

Female patient with gastric Ca

Enzymatic isolation of autologous tumor cells from the primary tumor

Isolation of PBMC directly after tumor resection during the OP

Stimulation Batch:

50 µg of trifunctional antibody/ml of medium anti-EpCAM x anti-CD3 (isotype combination mouse IgG2a x rat IgG2b)

$1.0 \times 10^6$ PBMC/ml $5.0 \times 10^4$ autologous tumor cells in suspension during stimulation Stimulation over 12 h Measurement method:

Direct cytotoxicity assay (BCECF fluorescence release assay)

Incubation time 12 h

Interpretation:

PBMCs were removed during the OP after resection of the gastric Ca (=point in time of the immunosuppression due to the operation). At the same time preparation of an autologous individual cell suspension. After stimulation with trAb and target cells, the PBMCs removed during the OP are capable of effectively destroying autologous tumor cells. On the other hand, allogenic EpCAM-negative tumor cells are not destroyed. This effect surprisingly functions directly after the operation, that is to say in an immunosuppressive situation.

Figure 1:
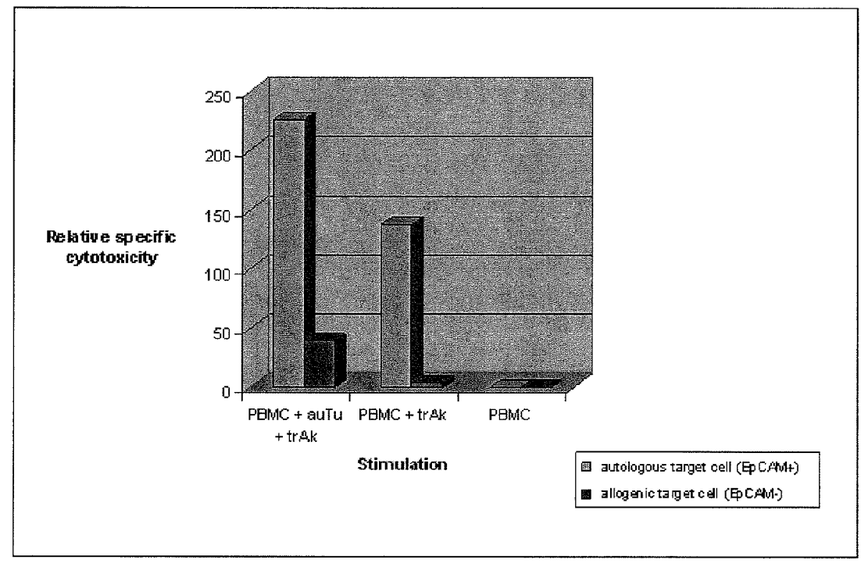

The attached FIG. 1 illustrates these actions. The figure shows:

Stimulation Batches:

PBMC+trifunctional antibody+autologous EpCAM+target cells

PBMC+trifunctional antibody

PBMC

4. Embodiment Example

In a phase II study, the adjuvant treatment of patients during surgical treatment of a gastric carcinoma combined with an intraoperative administration of the trifunctional antibody catumaxomab was compared with a treatment of such patients without intraoperative administration of the antibody.

55 randomised gastric carcinoma patients (T2b/T3/T4, N+/−, MO) in total were treated during a surgical D2 intervention, either exclusively with a surgical intervention or with an intraoperative administration of the trifunctional antibody catumaxomab. An intraoperative intraperitoneal infusion and 4 postoperative interperitoneal infusions with increasing doses, on day 7, 10, 13 and 16, were administered. The primary aims were safety, tolerability and feasibility.

Catumaxomab is an anti-EpCAM x anti-CD3 trifunctional monoclonal antibody with 2 different specificities, which can bind simultaneously to the epithelial cell adhesion molecule EpCAM on tumor cells and the CD3 antigen on T cells. The Fc region comprises the immunoglobulin isotypes mouse $IgG_{2a}$ and rat $IgG_{2b}$, which can preferentially bind FcγI and III receptors on accessory cells, for example macrophages, dendritic cells and NK cells, but not to the inhibitory FcγIIb receptor, which is expressed on B cells.

Of the 55 patients treated, 27 were treated exclusively by surgery, and 28 with an intraoperative administration of the antibody. The presence of the target antigen EpCAM was confirmed in 100% of the patients. 78% (22/28) of the patients treated with the antibody received all 5 infusions. 40% of the treatment-emergent adverse events (TEAEs) occurred directly after the intraoperative administration. TEAEs (CTC grade≥3) occurred in 22 patients (control: 10 patients). The most frequent TEAEs in the catumaxomab group were anaemia, pyrexia, SIRS and abdominal pain. All the serious TEAEs relating to these subsided after the end of the treatment, with the exception of a nephropathy in one patient, in whom mild late symptoms still remained. There was no trend towards an accumulation of serious side effects or complications (e.g. in wound healing) compared with those patients who were treated only by surgery.

Summarising, it can be said that the adjuvant intraoperative treatment of gastric carcinomas in which a trifunctional antibody is applied directly locally into the abdominal cavity during the operation was tolerated surprisingly excellently by the patients. This treatment form therefore opens up a novel possibility for avoiding the reoccurrence of intraabdominal tumors in patients following surgical removal of the gastric carcinoma, caused by dissemination of the tumor cells.

What is claimed is:

1. A method for destroying tumor cells, the method comprising:

Administering directly and locally into a human patient's abdominal cavity, during surgical removal of a tumor located in the patient's abdominal cavity, a pharmaceutical composition comprising a trifunctional, bispecific and/or trispecific antibody, wherein the trifunctional, bispecific and/or trispecific antibody binds to a T cell via CD3;

binds to at least one tumor-associated antigen which is expressed on the tumor cells; and binds by its Fc part (in the case of bispecific antibodies) or by a third specificity (in the case of trispecific antibodies) to Fc receptor-positive cells, wherein the antibody is administered in an amount of about 1 to about 400 µg.

2. The method according to claim 1, wherein the pharmaceutical composition comprises a physiologically acceptable medium designed for application into the abdominal cavity.

3. The method according to claim 2, wherein the medium containing the antibody remains in the abdominal cavity for a period of time which is sufficient to establish contact between the antibody and disseminated tumor cells and the medium is then removed again with the antibody, or the medium remains in the abdominal cavity with the antibody and is absorbed there.

4. The method according to claim 1, wherein the antibody is administered in an amount of about 5 to about 100 µg.

5. The method according to claim 1, wherein the antibody is directed against a tumor antigen chosen from the group consisting of Her2/neu, CD20, CD30, EpCAM, G250, proteoglycans, GD2, GD3, MHC II, EGF-R, CA125 and CEA.

6. The method according to claim 1, wherein the antibody binds to type I and/or type III Fc-γ receptor-positive cells via its Fc content.

7. The method according to claim 1, wherein the antibody is an anti-CD3 X anti-tumor-associated antigen bispecific antibody.

8. The method according to claim 1, wherein the antibody is a bispecific antibody chosen from a group consisting of a heterologous bispecific antibody and a heterologous rat/mouse bispecific antibody.

9. The method according to claim 1, wherein the antibody comprises an isotype combinations in the Fc region which is selected from the group consisting of:

rat IgG2b/mouse IgG2a, rat IgG2b/mouse IgG2b, rat IgG2b/human IgG1, and rat IgG2b/human IgG2.

10. The method according to claim 1, wherein the antibody has the following isotype combination:

mouse [VH-CH1, VL-CL]-human IgG1-[hinge]-human IgG1-[CH2-CH3]/rat [VH-CH1, VL-CL]-human IgG1-[hinge]-human IgG3 [Caucasian allotypes G3m(b+g) =no binding to protein A]-[CH2-CH3];

and/or the antibody is an anti-Her2/neu x anti-CD3 antibody or an anti-EpCAMx anti-CD3 antibody which binds to type I/III Fc-γ receptors, with the isotype combination rat IgG2b/mouse IgG2a.

11. The method according to claim 1, further comprising administering the trifunctional, bispecific or trispecific antibody postoperatively in at least one further dose.

12. The method according to claim 11, wherein the antibody is administered postoperatively in a second dose and third dose.

13. The method according to claim 11, wherein the antibody is administered postoperatively as the second dose in an amount of about 1 to about 20 µg, a subsequent dose in an amount of about 20 to about 100 µg, and any further subsequent administration in an amount of about 100 to about 500 µg.

14. The method according to claim 11, wherein the antibody is administered postoperatively in an amount of about 5 to about 1,000µg, intraperitoneally, and wherein the postoperative administration is carried out 2-5 times.

15. The method according to claim 1, wherein the antibody is administered in an amount of about 10 to about 50 µg.

16. The method according to claim 1, wherein the antibody is further administered postoperatively as the second dose in an amount of in an amount of about 5 to about 10 µg, a subsequent dose in an amount of about 30 to about 60 µg, and any further subsequent administration in an amount of about 100 to about 300 µg.

17. The method according to claim 1, wherein the antibody is further administered postoperatively and intraperitoneally in an amount of about 10-500 µg, and wherein the postoperative administration is carried out 2-5 times.

18. The method according to claim 1, wherein the antibody is further administered postoperatively and intraperitoneally in an amount of about 10 to about 150 µg, and wherein the postoperative administration is carried out 2-5 times.

19. The method according to claim 11, wherein the postoperative administration takes place 48-72 hours after the tumor is surgically removed.

20. The method according to claim 11, wherein the postoperative administration continues over a period of up to 12-20 days.

* * * * *